United States Patent [19]

Gutierrez

[11] Patent Number: 4,592,356
[45] Date of Patent: Jun. 3, 1986

[54] LOCALIZING DEVICE

[76] Inventor: Pedro Gutierrez, 141 Old Short Hills Rd., Apt. 125, West Orange, N.J. 07052

[21] Appl. No.: 655,414

[22] Filed: Sep. 28, 1984

[51] Int. Cl.⁴ .............................................. A61B 17/06
[52] U.S. Cl. ................................. 128/339; 128/334 R; 128/335
[58] Field of Search ............... 128/303 R, 314, 329 R, 128/329 A, 334 R, 339; 227/DIG. 1; 502/335

[56] References Cited

U.S. PATENT DOCUMENTS 3,308,819 3/1967 Arp .................................. 604/164 X
4,114,618 9/1978 Vargas .................................. 604/165

OTHER PUBLICATIONS

Usefulness of Mammographic Localizing Wire in Resecting Palpable Lesions of the Breast by Arlene M. Weinshelbaum, M.D., and Edward I. Weinshelbaum, M.D. F.A.C.S., Department of Radiology, University of Florida, College of Medicine, Gainesville Veterans Administration Medical Center and Alachua General Hospital.

Primary Examiner—W. J. Shine
Attorney, Agent, or Firm—Elliot M. Olstein

[57] ABSTRACT

Localizing needle having anchor-like barbs to firmly anchor the needle in skin or tissue so as to aid in location of lesions.

8 Claims, 2 Drawing Figures

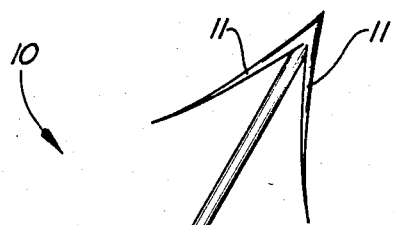
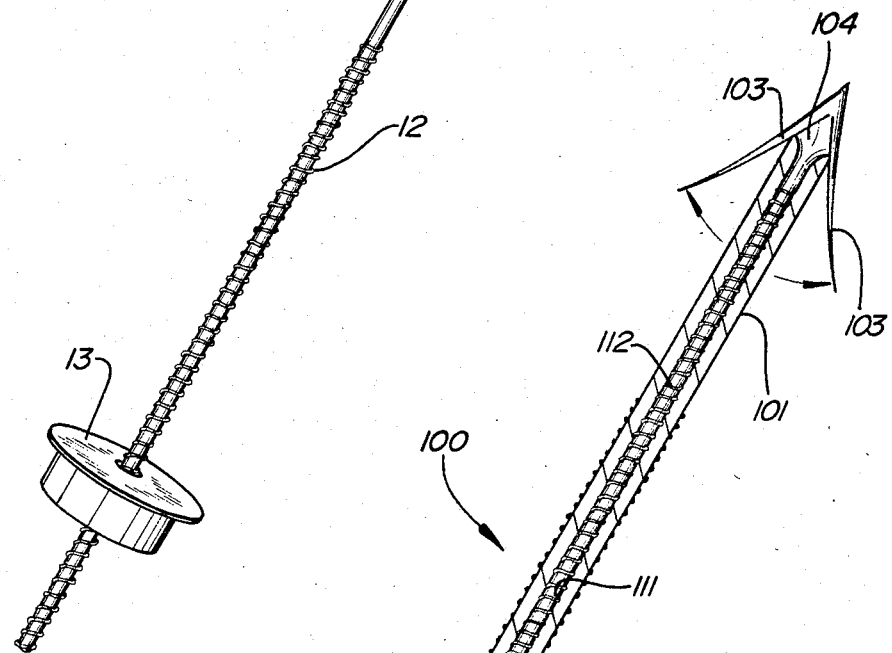

LOCALIZING DEVICE

This invention relates to a medical device and more particularly to a localizing device useful in operative procedures.

In many cases it is necessary for a surgeon to localize a portion of tissue or foreign matter in the tissue which is to be removed in an operative procedure so as to facilitate the location of the matter to be removed.

It has been proposed to use a wire with a hooked tip for localizing both palpable and occult lesions; for example, "Usefulness of Mammographic Localizing Wire in resecting Palpable Lesions of the Breast", Weinshelbaum, et al. Such a device, however, is easily dislodged, and in addition, it is difficult to localize the wire in the tissue. Thus, for example, there is a need for a device to localize nonpalpable lesions of the breast found by mammography.

In accordance with the present invention, there is provided an improved localizing device for insertion into tissue which is comprised of a needle having at one end thereof anchoring means for firmly anchoring the needle in the tissue, and a clamping means at the other end thereof securing the needle on the skin surface.

In accordance with a preferred embodiment, the anchor means is in the form of at least two barbs at the end of the needle for firmly anchoring the needle in the tissue.

The needle has dimensions such that it can be easily located at both skin and lesion levels, and is sufficiently rigid so that it remains in place. In general, the needle has a thickness of at least 1.0 mm. In most cases, the thickness of the needle is no greater than 2.0 mm. In general, the length of the needle is from 2.0 to 8.0 cm.

The anchor means in the form of at least two barbs may be constructed in a manner such that the at least two barbs are movable toward and away from the body of the needle (expansion and contraction of the barbs) so as to facilitate insertion, anchoring and removing of the localizing needle.

BRIEF DESCRIPTION OF THE DRAWINGS

The invention will be further described with respect to the accompanying drawings, wherein:

FIG. 1 is a view in elevation of an embodiment of a localizing device in accordance with the present invention; and FIG. 2 is an elevational view of another embodiment of a localizing device in accordance with the present invention.

Referring now to FIG. 1 of the drawing, there is shown a localizing device in the form of a needle 10 having an anchor means at one end thereof in the form of two barbs 11.

The distal end of the needle 10 includes screws threads, which as particularly shown, extend over about two-thirds of the needle, with such threads being generally designated as 12. The threads 12 are for a movable clamp, designated as 13, whereby the clamp 13 may be positioned at a desired point on the distal end of the needle 10.

The clamp 13 functions to firmly maintain the needle 10 in place after insertion into the skin and tissue by moving the clamp 13 along the threads 12 until it comes into contact with the skin surface. The combination of the two barbs 11 and the screw clamp 13 functions to maintain the localizing needle 10 firmly positioned in the tissue so as to aid a surgeon during a surgical procedure.

Another embodiment of the present invention is shown in FIG. 2 of the drawings wherein the localizing device, in the form of a needle 100, is comprised of an outer tube 101 and an inner rod 102 which has an anchor means at one end thereof in the form of two barbs 103. The barbs 103 are connected to the rod 102 by flexible struts or vanes 104 so as to permit collapsing of the barbs 103 against the tube 101 and expansion of the barbs 103 away from the tube 101 so as to facilitate insertion, anchoring and removal of the localizing device.

The tube 101 includes a central threaded bore 111 for receiving the rod 102 which has external screw threads 112. The distal end of rod 102 includes a knob 113 for rotating the rod 102 relative to the tube 101. Rotation of the rod 102 into the tube 101 collapses the bars 103 against the tube 101, and rotation of the rod 102 out of tube 101 expands the barbs 103 away from the tube 101.

The distal end of the tube 101 is also provided with external threads for receiving a clamp (not shown) as in the embodiment of FIG. 1 so as to firmly maintain the needle 100 after insertion of the needle into the skin and tissue.

In using the device shown in FIG. 2, the needle is inserted into the skin or tissue with the barbs 103 collapsed against the tube 101, and after being inserted, the barbs 103 are expanded to anchor the needle in the skin or tissue. When the needle is to be removed, the barbs 103 are collapsed against the tube 101 to facilitate removal of the needle.

Although the invention has been described with respect to a specific mechanism for collapsing and expanding the barbs, it is to be understood that other mechanisms could be used within the spirit and scope of the invention. For example, a sliding internal rod could be employed instead of a screw mechanism as shown. Alternatively, the barbs can be spring loaded for expansion and contraction. The above mechanisms and others should be apparent to those skilled in the art from the teachings therein.

Similarly, although the invention has been particularly described with respect to the use of two anchor-like barbs, it is to be understood that more than two barbs may be employed.

In use, after choosing the area to be localized by the needle, the skin surface is prepped with a routine prepping solution, and a small amount of local anesthetic is applied to the skin. The needle is then inserted through the skin and aimed at the area where the suspected lesion is to be found. A mammogram or other means of diagnosis is repeated and if satisfied with the placement, the needle is clamped to the skin surface by the clamping means.

The needle does not need to be inserted directly in the lesion, it can be placed in a nearby area or be used as a fixed point of reference.

The present invention is particularly advantageous in that the localizing device is firmly anchored in the tissue. In addition, as a result of its dimensions, it is easy to localize the needle at both the skin and lesion levels. The localizing device may be easily inserted into tissue, such as the breast, and directed into the area of the suspected lesion. Once the needle is in the correct position, it is adequately affixed at both ends, with one end being affixed by the at least one barbs, and the other end by the screw clamp.

Since the needle has sufficient rigidity and size, it is easily located while further providing the advantage of not being easily moved prior and during the operative procedure.

These and other advantages should be apparent to those skilled in the art from the teachings herein.

Numerous modifications and variations of the present invention are possible in light of the above teachings and, therefore, within the scope of the appended claims, the invention may be practiced otherwise then as particularly described.

What is claimed is:

1. A localizing device comprising:
    a needle for insertion into tissue, said needle including anchoring means at one end thereof for anchoring the needle in the tissue; and clamp means positioned at the other end of the needle for securing the needle at the outer skin surface.

2. The device of claim 1 wherein the anchoring means for the needle is comprised of at least two barb means.

3. The device of claim 2 wherein the at least two barb means are flexible.

4. The device of claim 3 and further comprising means for collapsing and expanding the at least two barb means towards and away from the needle.

5. The device of claim 2 wherein the needle has a thickness of at least 1.0 mm.

6. The device of claim 5 wherein the thickness is no greater than 2.0 mm.

7. The device of claim 2 wherein said clamp means is comprised of threads on the needle at the end opposite said anchoring means, and a movable clamp means received by said threads.

8. The device of claim 7 wherein the needle has a thickness of at least 1.0 mm. and no greater than 2.0 mm.

* * * * *